United States Patent [19]

Krimm et al.

[11]  4,252,737

[45]  Feb. 24, 1981

[54] PROCESS FOR THE PRODUCTION OF AROMATIC CARBONIC ACID ESTERS

[75] Inventors: Heinrich Krimm; Hans-Josef Buysch; Hans Rudolph, all of Krefeld, all of Fed. Rep. of Germany

[73] Assignee: Bayer Aktiengesellschaft, Leverkusen, Fed. Rep. of Germany

[21] Appl. No.: 110,942

[22] Filed: Jan. 10, 1980

Related U.S. Application Data

[63] Continuation of Ser. No. 931,563, Aug. 7, 1978, abandoned.

[30] Foreign Application Priority Data

Aug. 10, 1977 [DE] Fed. Rep. of Germany ....... 2736063

[51] Int. Cl.$^3$ ............................................ C07C 68/08
[52] U.S. Cl. ..................................... 260/463; 203/52; 203/70
[58] Field of Search .................... 260/463; 203/52, 70

[56] References Cited

U.S. PATENT DOCUMENTS

| | | | |
|---|---|---|---|
| 2,406,561 | 8/1946 | Rehberg | 203/52 |
| 3,011,954 | 12/1961 | Halpern et al. | 203/70 |
| 3,239,572 | 3/1966 | Zinsstag | 203/70 |
| 3,431,181 | 3/1969 | Bouniot | 203/70 |

FOREIGN PATENT DOCUMENTS

| | | | |
|---|---|---|---|
| 2528412 | 1/1979 | Fed. Rep. of Germany | 260/463 |
| 772627 | 4/1957 | United Kingdom. | |
| 808488 | 2/1959 | United Kingdom. | |

Primary Examiner—Donald G. Daus
Assistant Examiner—M. C. Eakin
Attorney, Agent, or Firm—Connolly and Hutz

[57] ABSTRACT

A process for the production of aromatic carbonic acid esters by transesterifying a mixture of dimethylcarbonamate/methanol and a methanol-immiscible azeotrope former for methanol with phenols in the presence of transesterification catalysts.

4 Claims, No Drawings

PROCESS FOR THE PRODUCTION OF AROMATIC CARBONIC ACID ESTERS

This application is a continuation of application Ser. No. 931,563 filed Aug. 7, 1978 now abandoned.

This invention relates to a process for the production of aromatic carbonic acid esters by transesterifying dimethyl carbonate with phenols.

The transesterification of aliphatic carbonic acid esters with phenols in the presence of strong bases or alkali metal compounds is known from German Patent Specification Nos. 971,790 (=GB-PS No. 772,627); 1,020,184 (=GB-PS No. 808,489); 1,026,958 and 1,031,512 (=GB-PS No. 808,488). Transesterification reactions catalysed in this way have the disadvantage that they are not selective enough and thus considerable quantities of carbon dioxide are liberated in a secondary reaction.

The German Offenlegungsschrift No. 2,528,412 describes a transesterification process for the production of aromatic carbonic acid esters in the presence of Lewis acids, i.e. transition metal halides, or the corresponding acyloxy, alkoxy or aryloxy compounds as catalysts. Where dimethyl carbonate is used as a starting material in this process, an elaborate purifying and separating operation has to be carried out before in order to recover pure dimethyl carbonate (U.S. Pat. No. 3,803,201; German Pat. No. 2,450,856 and German Offenlegungsschrift No. 2,607,003). This is because an approximately 30% by weight azeotrope with methanol is formed in conventional processes for the production of dimethyl carbonate (U.S. Pat. No. 3,642,858 and German Offenlegungsschrift No. 2,615,665).

Accordingly, it is an object of the present invention to provide a transesterification process which enables to use this azeotrope or any other mixture of dimethyl carbonate and methanol. Preferably the concentration of dimethyl carbonate in methanol reaches from 95 to 10% by weight. The 30% by weight azeotrope is preferably used.

According to the present invention, this object can be achieved by using methanol-immiscible azeotrope formers for methanol.

Accordingly, the present invention relates to a process for the production of aromatic carbonic acid esters by transesterifying dimethyl carbonate with phenols, under the simultaneous elimination of methanol in the presence of transesterification catalysts, wherein mixtures of dimethyl carbonate/methanol and methanol-immiscible azeotrope formers for methanol are used for the reaction.

Azeotrope formers suitable for the inventive process are, preferably, saturated aliphatic $C_5$-$C_8$-hydrocarbons having a boiling point in the range of from 40° to 130° C., such as pentane, hexane, heptane, octane and isooctane, and also commercial gasoline fractions which predominantly contain the above-mentioned hydrocarbons, such as petroleum ether, ligroin and light gasoline, and also mixtures of the above-mentioned hydrocarbons. The azeotrope formers are used in such quantities that the methanol of the starting dimethyl carbonate/methanol mixture and that formed during the transesterification reaction can be distilled off. The required amount of azeotrope former can be found in the known tables of the various azeotrope compositions (in the Handbook of Chemistry and Physics 51st Edition, 1970 of the Rubber Comp., Cleveland/Ohio) or can be determined in a simple test. An excess of azeotrope former can be used, but should be as low as possible because of economic reasons.

Using the process according to the present invention, it is surprisingly possible to separate off the azeotrope consisting of the methanol formed during the transesterification reaction and one of the above-mentioned hydrocarbons, although it is known that these hydrocarbons also form azeotrope-boiling mixtures with dimethyl carbonate. The process according to the invention gives substantially the same yields as the previously known processes without the necessity to isolate the dimethyl carbonate before the transesterification reaction.

Suitable phenols for the use in the inventive process are, preferably, compounds corresponding to the following general formula:

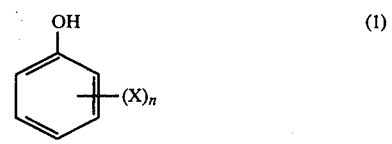

wherein X represents hydrogen, a $C_1$-$C_3$-alkyl radical, a halogen atom, preferably chlorine, or a nitro group; and n represents 1 or 2.

It is particularly preferred to use phenol, o,m,p-cresol, o,m,p-chlorophenol, o,m,p-ethyl phenol, o,m,p-propyl phenol, o,m,p-nitrophenol, 2,6-dimethylphenol, 2,4-dimethyl phenol or 3,4-dimethyl phenol.

Instead of monohydric phenols, it is also possible to use bisphenols, such as dihydroxy diaryl alkanes containing from 1 to 4 carbon atoms in the alkyl radical, for example bisphenol A.

Suitable catalysts are various transesterification catalysts. Preferred catalysts of this type are alkali metal compounds, such as lithium, sodium, and potassium hydroxides, alcholates, phenolates, carboxylates and carbonates. Other preferred catalysts are organo tin compounds, such as trimethyl tin acetate, triethyl tin benzoate, tributyl tin acetate, triphenyl tin acetate, dibutyl tin acetate, dibutyl tin dilaurate, dioctyl tin dilaurate, dibutyl tin adipate, methoxy tributyl tin, methoxy triphenyl tin, phenoxy triethyl tin, dimethyl dibutyl tin, dimethyl tin glycolate, diethoxy dibutyl tin, diphenoxy dibutyl tin, dimethoxy diphenyl tin, triethyl tin hydroxide, triphenyl tin hydroxide, hexa-ethyl stannoxane, hexabutyl stannoxane, tetrabutyl diphenoxy stannoxane, dibutyl tin oxide and dioctyl tin oxide and titanium compounds of the tetrabutyl or tetraphenyl titanate type.

The catalysts are used preferably in concentrations of from 0.001 to 20% by weight, based on the reaction mixtures as a whole. The ratio by weight of dimethyl carbonate to phenol may fluctuate within wide limits and may be from 1:99 to 99:1, preferably from 1:9 to 9:1. This ratio determines whether aryl methyl carbonate or diaryl carbonate predominates in the end product.

The methylaryl carbonate formed in addition to diaryl carbonate may be readily separated off by distillation and may either be reacted with fresh phenol or returned for further reaction following separation of the diaryl carbonate.

The reaction temperature is preferably in the range of from 50° to 250° C. and, with particular preference, in the range of from 100° to 200° C. The reaction is preferably carried out under a pressure of from 1 Torr to 20 atms. and more preferably under a pressure of from 1 to 5 atms.

The inventive process is preferably carried out by heating the transesterification mixture to the required reaction temperature in a relatively long column, separating off the methanol as it is released from the reaction mixture together with the azeotrope former, optionally by means of an inert gas stream, and delivering dimethyl carbonate with the azeotrope former to the lower parts of the column in a quantity commensurate with the reduction of the concentration of both substances in the reaction mixture.

The aromatic carbonates obtained by the inventive process may be reacted by a known method to form polycarbonates, or may be used as plant protection agents.

EXAMPLE (a) In a 2.9 meter high metallised column packed with glass rings, 940 g (10 moles) of phenol, 150 g of 30% dimethyl carbonate/methanol azeotrope (0.5 mole), 100 g of n-heptane and 2 g of tetrabutyl titanate are heated in such a way that a two-phase azeotrope consisting essentially of heptane and methanol can be removed at from 58° to 59° C. During the 45-hour reaction, a quantity of dimethyl carbonate and heptane corresponding to the methanol/heptane mixture distilled off is added at the middle of the column in such a way that the sump temperature amount to 160° C. In this way, a total of 340 g of dimethyl carbonate/methanol azeotrope with 400 g of heptane is used, corresponding to 1.13 mole of dimethyl carbonate. The reaction product is fractionated in a 1 meter high column. After first runnings consisting of methanol, dimethyl carbonate and heptane, 887 g of unreacted phenol, 30.6 g of methyl phenyl carbonate and 32.5 g of diphenyl carbonate distill over at 69° to 74° C./8 Torr, 83°-93° C./8 Torr and 146°-160° C./8 Torr, respectively. Accordingly, the yield of aromatic carbonates, based on reacted phenol, amounts to 94% of the theoretical yield.

(b) A mixture of 45.6 g (0.2 mole) of 2,2-bis-(4-hydroxyphenyl)-propane, 47.1 g (0.22 mole) of the diphenyl carbonate produced as described in part (a) and 0.008 g of sodium methylate is slowly heated to 210° C. under a pressure of 20 Torr, most of the eliminated phenol distilling off. The pressure is then reduced to 0.2 Torr and the temperature increased over a period of 1 hour to 250° C., and over a period of another 2 hours to 280° C., until the melt has become so viscous that it can hardly be stirred. A clear, colourless and elastic plastic is obtained on cooling. This plastic can be processed from the melt to form mouldings having excellent strength properties.

We claim:

1. A process for the production of aromatic carbonic acid esters by transesterification comprising
   (a) mixing a phenol, dimethyl carbonate, methanol, a transesterification catalyst and a methanol-immiscible hydrocarbon azeotrope former for methanol selected from the group consisting of pentane, hexane, heptane, octane, isooctane, and mixtures thereof;
   (b) transesterifying the dimethyl carbonate with the phenol; and
   (c) simultaneous with (b) removing methanol by distilling off the methanol/hydrocarbon azeotrope.

2. A process according to claim 1 wherein the source of dimethyl carbonate and methanol mixed in (a) is a mixture of 10-95% dimethyl carbonate with the remainder methanol.

3. A process according to claim 2 wherein the dimethyl carbonate/methanol mixture is a dimethyl carbonate/methanol azeotrope containing about 30% dimethyl carbonate.

4. A process as claimed in claim 1, wherein the transesterification is carried out at temperature of from 50° to 250° C.

* * * * *